United States Patent [19]

Hotz et al.

[11] 4,097,491

[45] Jun. 27, 1978

[54] N-DIALKOXYALKYL-N-DIOXANALKYLENE-α-HALOALKANAMIDES

[75] Inventors: Roger D. Hotz, Evanston; Leonard J. Stach, Riverside, both of Ill.; Sidney B. Richter, Barberton, Ohio

[73] Assignee: Velsicol Chemical Corporation, Chicago, Ill.

[21] Appl. No.: 805,254

[22] Filed: Jun. 10, 1977

[51] Int. Cl.$^2$ .................. C07D 319/04; A01N 9/24
[52] U.S. Cl. ........................ 260/340.7; 71/88
[58] Field of Search .................... 260/340.7

[56] References Cited

U.S. PATENT DOCUMENTS

| | | | |
|---|---|---|---|
| 3,736,112 | 5/1973 | Abramitis et al. | 71/88 X |
| 3,888,882 | 6/1975 | Richter et al. | 260/340.7 |
| 3,946,043 | 3/1976 | Richter et al. | 260/340.7 |

Primary Examiner—Ethel G. Love

Attorney, Agent, or Firm—Robert M. Phipps; Robert J. Schwarz; Dietmar H. Olesch

[57] ABSTRACT

This invention discloses new chemical compounds of the formula

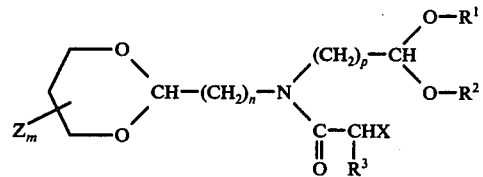

wherein Z is alkyl; m is an integer from 0 to 4; n and p are each integers from 1 to 2; $R^1$ and $R^2$ are each alkyl; $R^3$ is hydrogen or alkyl; and X is halogen. The compounds of the foregoing description are useful as herbicides.

9 Claims, No Drawings

N-DIALKOXYALKYL-N-DIOXANALKYLENE-α-HALOALKANAMIDES

This invention relates to new compositions of matter and more specifically relates to new chemical compounds of the formula

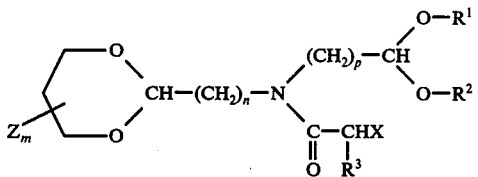

wherein Z is alkyl; m is an integer from 0 to 4; n and p are each integers from 1 to 2; $R^1$ and $R^2$ are each alkyl; $R^3$ is hydrogen or alkyl; and X is halogen.

The compounds of the present invention are useful as herbicides and are particularly suitable as preemergence grass herbicides. Moreover the subject compounds are useful for stunting the growth of ornamental turf, reducing the need for mowing.

In a preferred embodiment of the present invention Z is lower alkyl; m is an integer from 0 to 2; n and p are each integers from 1 to 2; $R^1$ and $R^2$ are each lower alkyl; $R^3$ is hydrogen or lower alkyl; and X is chlorine or bromine.

The term lower as used herein designates a straight or branched carbon chain of up to six carbon atoms.

The compounds of the present invention can be prepared by reacting a compound of the formula

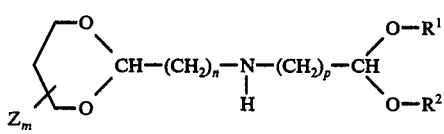

wherein Z, m, n, p, $R^1$ and $R^2$ are as heretofore described, with an α-haloalkanoyl chloride of the formula

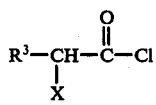

wherein $R^3$ and X are as heretofore described. This reaction can be effected by combining a compound of formula II with an about equimolar or slight excess molar amount of a compound of formula III in an inert organic reaction medium, such as benzene, in the presence of an acid acceptor, such as an alkali metal carbonate or bicarbonate or a tertiary amine, at a temperature of about −10° to about 25° C and stirring the resulting mixture for a period of from about 15 to about 120 minutes. After this time the reaction mixture can be washed with water to remove inorganic salts and stripped of solvent to yield the desired product. This product can then be used as such or can be further purified by conventional means.

The compounds of formula II can be prepared by reacting a substituted amine of the formula

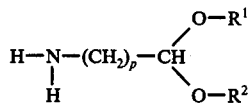

wherein $R^1$ and $R^2$ are as heretofore described with a compound of the formula

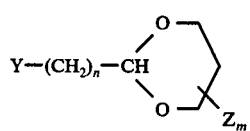

wherein Y is chlorine or bromine and n, Z and m are as heretofore described. This reaction can be effected by combining the compound of formula V with an equimolar or excess molar amount of the amine of formula IV in the presence of an acid acceptor such as a tertiary amine and heating the mixture with agitation for a period of from about 4 to 24 hours. After this time the reaction mixture can be filtered to remove acid acceptor salt. The filtrate can then be distilled under reduced pressure to yield the desired product.

The compounds of formula V when not readily available can be prepared by reacting an acetal of the formula

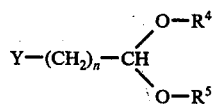

wherein Y and n are as heretofore described and $R^4$ and $R^5$ are methyl or ethyl, with a diol of the formula

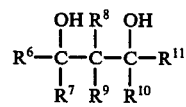

wherein $R^6$, $R^7$, $R^8$, $R^9$, $R^{10}$ and $R^{11}$ are each hydrogen or alkyl provided a maximum of four of $R^6$, $R^7$, $R^8$, $R^9$, $R^{10}$ and $R^{11}$ are alkyl. This reaction can be effected by combining the compound of formula VI with the compound of formula VII in about equimolar amounts and in the presence of an acid catalyst such as sulfuric acid or toluene sulfonic acid under anhydrous conditions. The mixture can be heated for a period of from 1 to about 4 hours or until no more alcohol is given off. After this time the reaction mixture can be distilled under reduced pressure to yield the desired product.

Exemplary suitable diols of formula VII for preparing the compounds of the present invention are propandiol-1,3, butandiol-1,3, pentandiol-1,3, hexandiol-1,3, heptandiol-1,3, octandiol-1,3, hexandiol-2,4, octandiol-2,4, pentandiol-2,4, octandiol-3,5, 3-methylbutandiol-1,3, 3,3-dimethylbutandiol-1,3 and the like.

Exemplary suitable amines of formula IV are 2,2-dimethoxyethylamine, 2,2-diethoxyethylamine, 2-ethoxy-2-methoxyethylamine, 2-methoxy-2-propoxyethylamine, 2,2-dipropoxyethylamine, 2,2-dibutoxyethylamine, 2,2-dihexyloxyethylamine, 3,3-dimethoxypropylamine, 3,3-dipropoxypropylamine, 3-methoxy-3-propoxypropylamine and the like.

Exemplary suitable α-haloalkanoyl chlorides of formula III for preparing the compounds of this invention are chloroacetyl chloride, α-chloropropanoyl chloride, α-bromobutanoyl chloride, α-chloropentanoyl chloride, α-chlorohexanoyl chloride, α-chloro-α-methylbutanoyl chloride, α-chloroheptanoyl chloride and the like.

EXAMPLE 1

Preparation of N-(2,2-Diethoxyethyl)-N-(1,3-dioxan-2-ylmethyl)amine 2,2-Diethoxyethylamine (23.3 grams), 2-bromomethyl-1,3-dioxane (29.2 grams), triethylamine (25 ml) and toluene (150 ml) are charged into a glass reaction vessel equipped with a mechanical stirrer, thermometer and reflux condenser. The reaction mixture is heated at reflux overnight. After this time the mixture is cooled and filtered. The filtrate is then distilled under reduced pressure to yield the desired product N-(2,2-diethoxyethyl)-N-(1,3-dioxan-2-ylmethyl)amine.

EXAMPLE 2

Preparation of N-(2,2-Diethoxyethyl)-N-(1,3-dioxan-2-ylmethyl-α-chloroacetamide

N-(2,2-Diethoxyethyl)-N-(1,3-dioxan-2-ylmethyl)-amine (4 grams), benzene (100 ml), water (100 ml) and sodium carbonate (2 grams) are charged into a glass reaction vessel equipped with a mechanical stirrer and thermometer. The mixture is cooled to a temperature of 5° to 10° C and chloroacetyl chloride (1.5 ml) is added dropwise with stirring. After the addition is completed stirring is continued until the reaction mixture reaches room temperature. After this time the organic phase is separated from the aqueous phase and is washed with water. The washed solution is then dried over anhydrous magnesium sulfate, filtered and stripped of solvent under reduced pressure to yield the desired product N-(2,2-diethoxyethyl)-N-(1,3-dioxan-2-ylmethyl)-α-chloroacetamide as the residue.

EXAMPLE 3

Preparation of N-(2,2-Dipropoxyethyl)-N-(4-methyl-1,3-dioxan-2-ylmethyl)amine 2,2-Dipropoxyethylamine (0.11 mole), 2-bromomethyl-4-methyl-1,3-dioxane (0.1 mole), triethylamine (20 ml) and toluene (150 ml) are charged into a glass reaction vessel equipped with a mechanical stirrer, thermometer and reflux condenser. The reaction is heated at reflux for a period of about 12 hours. After this time the reaction mixture is allowed to cool to room temperature and is filtered. The reaction mixture is then stripped of solvent and unreacted starting materials under reduced pressure to yield the desired product N-(2,2-dipropoxyethyl)-N-(4-methyl-1,3-dioxan-2-ylmethyl)amine.

EXAMPLE 4

Preparation of N-(2,2-Dipropoxyethyl)-N-(4-methyl-1,3-dioxan-2-ylmethyl)-α-chloroacetamide N-(2,2-Dipropoxyethyl)-N-(4-methyl-1,3-dioxan-2-yl-methyl)amine (0.05 mole), benzene (100 ml), water (100 ml) and sodium carbonate (2 grams) are charged into a glass reaction vessel equipped with a mechanical stirrer and thermometer. The reaction mixture is cooled to a temperature of from 5° to 10° C and chloroacetyl chloride (0.05 mole) is added dropwise with stirring. After the addition is completed stirring is continued until the reaction mixture has reached room temperature. After this time the organic phase is separated from the aqueous phase and is washed with water. The washed solution is then dried over anhydrous magnesium sulfate, filtered and stripped of solvent under reduced pressure to yield the desired product N-(2,2-dipropoxyethyl)-N-(4-methyl-1,3-dioxan-2-ylmethyl)-α-chloroacetamide as the residue.

EXAMPLE 5

Preparation of N-(2-Methoxy-2-ethoxyethyl)-N-(1,3-dioxan-2-ylmethyl)amine

2-Methoxy-2-ethoxyethylamine (0.11 mole), 2-bromomethyl-1,3-dioxane (0.1 mole), triethylamine (20 ml) and toluene (150 ml) are charged into a glass reaction vessel equipped with a mechanical stirrer, thermometer and reflux condenser. The reaction is heated at reflux for a period of about 12 hours. After this time the reaction mixture is allowed to cool to room temperature and is filtered. The reaction mixture is then stripped of solvent and unreacted starting materials under reduced pressure to yield the desired product N-(2-methoxy-2-ethoxyethyl)-N-(1,3-dioxan-2-ylmethyl)amine.

EXAMPLE 6

Preparation of N-(2-Methoxy-2-ethoxyethyl)-N-(1,3-dioxan-2-ylmethyl)-α-chloroacetamide N-(2-Methoxy-2-ethoxyethyl)-N-(1,3-dioxan-2-ylmethyl)-amine (0.05 mole), benzene (100 ml), water (100 ml) and sodium carbonate (2 grams) are charged into a glass reaction vessel eqiuipped with a mechanical stirrer and thermometer. The reaction mixture is cooled to a temperature of from 5° to 10° C and chloroacetyl chloride (0.05 mole) is added dropwise with stirring. After the addition is completed stirring is continued until the reaction mixture has reached room temperature. After this time the organic phase is separated from the aqueous phase and is washed with water. The washed solution is then dried over anhydrous magnesium sulfate, filtered and stripped of solvent under reduced pressure to yield the desired product N-(2-methoxy-2-ethoxyethyl)-N-(1,3-dioxan-2-ylmethyl)-α-chloroacetamide as the residue.

EXAMPLE 7

Preparation of N-(2,2-Dibutoxyethyl)-N-(4,5-dimethyl-1,3-dioxan-2-ylmethyl)amine 2,2-Dibutoxyethylamine (0.11 mole), 2-bromoethyl-4,5-dimethyl-1,3-dioxane (0.1 mole), triethylamine (20 ml) and toluene (150 ml) are charged into a glass reaction vessel equipped with a mechanical stirrer, thermometer and reflux condenser. The reaction is heated at reflux for a period of about 12 hours. After this time the reaction mixture is allowed to cool to room temperature and is filtered. The reaction mixture is then stripped of solvent and unreacted starting materials under reduced pressure to yield the desired product N-(2,2-dibutoxyethyl)-N-(4,5-dimethyl-1,3-dioxan-2-ylmethyl)-amine.

EXAMPLE 8

Preparation of
N-(2,2-Dibutoxyethyl)-N-(4,5-dimethyl-1,3-dioxan-2-ylmethyl)-α-chloroacetamide N-(2,2-Dibutoxyethyl)-N-(4,5-dimethyl-1,3-dioxan-2-ylmethyl)amine (0.05 mole), benzene (100 ml), water (100 ml) and sodium carbonate (2 grams) are charged into a glass reaction vessel equipped with a mechanical stirrer and thermometer. The reaction mixture is cooled to a temperature of from 5° to 10° C and chloroacetyl chloride (0.05 mole) is added dropwise with stirring. After the addition is completed stirring is continued until the reaction mixture has reached room temperature. After this time the organic phase is separated from the aqueous phase and is washed with water. The washed solution is then dried over anhydrous magnesium sulfate, filtered and stripped of solvent under reduced pressure to yield the desired product N-(2,2-dibutoxyethyl)-N-(4,5-dimethyl-1,3-dioxan-2-ylmethyl)-α-chloroacetamide as the residue.

EXAMPLE 9

Preparation of
N-(2,2-Dihexyloxyethyl)-N-(4-isopropyl-1,3-dioxan-2-ylethyl)amine 2,2-Dihexyloxyethyl (0.11 mole), 2-bromoethyl-4-isopropyl-1,3-dioxane (0.1 mole), triethylamine (20 ml) and toluene (150 ml) are charged into a glass reaction vessel equipped with a mechanical stirrer, thermometer and reflux condenser. The reaction is heated at reflux for a period of about 12 hours. After this time the reaction mixture is allowed to cool to room temperature and is filtered. The reaction mixture is then stripped of solvent and unreacted starting materials under reduced pressure to yield the desired product N-(2,2-dihexyloxyethyl)-N-(4-isopropyl-1,3-dioxan-2-ylethyl)amine.

EXAMPLE 10

Preparation of
N-(2,2-Dihexyloxyethyl)-N-(4-isopropyl-1,3-dioxan-2-ylethyl)-α-chloropropionanamide N-(2,2-Dihexyloxyethyl)-N-(4-isopropyl-1,3-dioxan-2-ylethyl)amine (0.05 mole), benzene (100 ml), water (100 ml) and sodium carbonate (2 grams) are charged into a glass reaction vessel equipped with a mechanical stirrer and thermometer. The reaction mixture is cooled to a temperature of from 5° to 10° C and α-chloropropionyl chloride (0.05 mole) is added dropwise with stirring. After the addition is completed stirring is continued until the reaction mixture has reached room temperature. After this time the organic phase is separated from the aqueous phase and is washed with water. The washed solution is then dried over anhydrous magnesium sulfate, filtered and stripped of solvent under reduced pressure to yield the desired product N-(2,2-dihexyloxyethyl)-N-(4-isopropyl-1,3-dioxan-2-ylethyl)-α-chloropropionanamide as the residue.

EXAMPLE 11

Preparation of
N-(3,3-Diethoxypropyl)-N-(4,5-dimethyl-1,3-dioxan-2-ylmethyl)amine 3,3-Diethoxypropylamine (0.11 mole), 2-bromomethyl-4,5-dimethyl-1,3-dioxane (0.1 mole), triethylamine (20 ml) and toluene (150 ml) are charged into a glass reaction vessel equipped with a mechanical stirrer, thermometer and reflux condenser. The reaction is heated at reflux for a period of about 12 hours. After this time the reaction mixture is allowed to cool to room temperature and is filtered. The reaction mixture is then stripped of solvent and unreacted starting materials under reduced pressure to yield the desired product N-(3,3-diethoxypropyl)-N-(4,5-dimethyl-1,3-dioxan-2-ylmethyl)amine.

EXAMPLE 12

Preparation of
N-(3,3-Diethoxypropyl)-N-(4,5-dimethyl-1,3-dioxan-2-ylmethyl-α-bromoacetamide N-(3,3-Diethoxypropyl)-N-(4,5-dimethyl-1,3-dioxan-2-ylmethyl)amine (0.05 mole), benzene (100 ml), water (100 ml) and sodium carbonate (2 grams) are charged into a glass reaction vessel equipped with a mechanical stirrer and thermometer. The reaction mixture is cooled to a temperature of from 5° to 10° C and bromoacetyl chloride (0.05 mole) is added dropwise with stirring. After the addition is completed stirring is continued until the reaction mixture has reached room temperature. After this time the organic phase is separated from the aqueous phase and is washed with water. The washed solution is then dried over anhydrous magnesium sulfate, filtered and stripped of solvent under reduced pressure to yield the desired product N-(3,3-diethoxypropyl)-N-(4,5-dimethyl-1,3-dioxan-2-ylmethyl)-α-bromoacetamide as the residue.

EXAMPLE 13

Preparation of
N-(2,2-Diethoxyethyl-N-(1,3-dioxan-2-ylmethyl-α-chlorobutanamide

N-(2,2-Diethoxyethyl)-N-(1,3-dioxan-2-ylmethyl)amine (0.05 mole), benzene (100 ml), water (100 ml) and sodium carbonate (2 grams) are charged into a glass reaction vessel equipped with a mechanical stirrer and thermometer. The reaction mixture is cooled to a temperature of from 5° to 10° C and α-chlorobutanoyl chloride (0.05 mole) is added dropwise with stirring. After the addition is completed stirring is continued until the reaction mixture has reached room temperature. After this time the organic phase is separated from the aqueous phase and is washed with water. The washed solution is then dried over anhydrous magnesium sulfate, filtered and stripped of solvent under reduced pressure to yield the desired product N-(2,2-diethoxyethyl)-N-(1,3-dioxan-2-ylmethyl-α-chlorobutanamide as the residue.

Additional compounds within the scope of the present invention can be prepared by the procedures of the foregoing examples.

Exemplary compounds are:
N-(2,2-dibutoxyethyl)-N-(5-ethyl-1,3-dioxan-2-ylmethyl)-α-chloroacetamide, N-(2,2-dipentyloxyethyl)-N-(5-propyl-1,3-dioxan-2-ylmethyl)-α-bromoacetamide, N-(3,3-dimethylpropyl)-N-(5-butyl-1,3-dioxan-2-ylmethyl)-α-bromopropionamide, N-(3,3-diethoxypropyl)-N-(4-pentyl-1,3-dioxan-2-ylmethyl)-α-bromobutanamide, N-(3,3-dipropoxypropyl)-α-(4-hexyl-1,3-dioxan-2-ylmethyl)-α-chloropentanamide, N-(3,3-dibutoxypropyl)-N-(1,3-dioxan-2-ylmethyl)-α-chlorohexanamide, N-(3,3-dipentyloxypropyl)-N-(1,3-dioxan-2-ylmethyl)-α-chloroheptanamide, N-(3,3-dihexyloxypropyl)-N-(5,5-dimethyl-1,3-dioxan-2-ylmethyl)-α-chloroacetamide, N-(2,2-diethoxyethyl)-N-(1,3-dioxan-2-ylmethyl)-α-chloroacetamide.

For practical use as herbicides the compounds of this invention are generally incorporated into herbicidal compositions which comprise an inert carrier and a herbicidally toxic amount of such a compound. Such herbicidal compositions, which can also be called formulations, enable the active compound to be applied conveniently to the site of the weed infestation in any desired quantity. These compositions can be solids such as dusts, granules, or wettable powders; or they can be liquids such as solutions, aerosols, or emulsifiable concentrates.

For example, dusts can be prepared by grinding and blending the active compound with a solid inert carrier such as the talcs, clays, silicas, pyrophyllite, and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water or oil to any desired concentration of the active compound, can be prepared by incorporating wetting agents into concentrated dust compositions.

In some cases the active compounds are sufficiently soluble in common organic solvents such as kerosene or xylene so that they can be used directly as solutions in these solvents. Frequently, solutions of herbicides can be dispersed under super-atmospheric pressure as aerosols. However, preferred liquid herbicidal compositions are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the weed infestation. The emulsifiers most commonly used in these concentrates are nonionic or mixtures of nonionic with anionic surface-active agents. With the use of some emulsifier systems an inverted emulsion (water in oil) can be prepared for direct application to weed infestations.

A typical herbicidal composition according to this invention is illustrated by the following example, in which the quantities are in parts by weight.

EXAMPLE 14

Preparation of a Dust

| Product of Example 2 | 10 |
| Powdered Talc | 90 |

The above ingredients are mixed in a mechanical grinder-blender and are ground until a homogeneous, free-flowing dust of the desired particle size is obtained. This dust is suitable for direct application to the site of the weed infestation.

The compounds of this invention can be applied as herbicides in any manner recognized by the art. One method for the control of weeds comprises contacting the locus of said weeds with a herbicidal composition comprising an inert carrier and as an essential active ingredient, in a quantity which is herbicidally toxic to said weeds, a compound of the present invention. The concentration of the new compounds of this invention in the herbicidal compositions will vary greatly with the type of formulation and the purpose for which it is designed, but generally the herbicidal compositions will comprise from about 0.05 to about 95 percent by weight of the active compounds of this invention. In a preferred embodiment of this invention, the herbicidal compositions will comprise from about 5 to about 75 percent by weight of the active compound. The compositions can also comprise such additional substances as other pesticides, such as insecticides, nematocides, fungicides, and the like; stabilizers, spreaders, deactivators, adhesives, stickers, fertilizers, activators, synergists, and the like.

The compounds of the present invention are also useful when combined with other herbicides and/or defoliants, dessicants, growth inhibitors, and the like in the herbicidal compositions heretofore described. These other materials can comprise from about 5 to about 95% of the active ingredients in the herbicidal compositions. Use of combinations of these other herbicides and/or defoliants, dessicants, etc., with the compounds of the present invention provide herbicidal compositions which are more effective in controlling weeds and often provide results unattainable with separate compositions of the individual herbicides. The other herbicides, defoliants, dessicants and plant growth inhibitors, with which the compounds of this invention can be used in the herbicidal compositions to control weeds, can include chlorophenoxy herbicides such as 2,4-D, 2,4,5-T, MCPA, MCPB, 4(2,4-DB), 2,4-DEB, 4-CPB, 4-CPA, 4-CPP, 2,4,5-TB, 2,4,5-TES, 3,4-DA, silvex and the like; carbamate herbicides such as IPC, CIPC, swep, barban, BCPC, CEPC, CPPC, and the like; thiocarbamate and dithiocarbamate herbicides such as CDEC, metham sodium, EPTC, diallate, PEBC, perbulate, vernolate and the like; substituted urea herbicides such as norea, siduron, dichloral urea, chloroxuron, cycluron, fenuron, monuron, monuron TCA, diuron, linuron, monolinuron, neburon, buturon, trimeturon and the like; symmetrical triazine herbicides such as simazine, chlorazine, atraone, desmetryne, norazine, ipazine, prometryn, atrazine, trietazine, simetone, prometone, propazine, ametryne and the like; chloroacetamide herbicides such as alpha-chloro-N,N-dimethylacetamide, CDEA, CDAA, alpha-chloro-N-isopropylacetamide, 2-chloro-N-isopropylacetanilide, 4-(chloroacetyl)morpholine, 1-(chloroacetyl)piperidine and the like; chlorinated aliphatic acid herbicides such as TCA, dalapon, 2,3-dichloropropionic acid, 2,2,3-TPA and the like; chlorinated benzoic acid and phenylacetic acid herbicides such as 2,3,6-TBA, 2,3,5,6-TBA, dicamba, tricamba, amiben, fenac, PBA, 2-methoxy-3,6-dichlorophenylacetic acid, 3-methoxy-2,6-dichlorophenylacetic acid, 2-methoxy-3,5,6-trichlorophenylacetic acid, 2,4-dichloro-3-nitrobenzoic acid and the like; and such compounds as aminotriazole, maleic hydrazide, phenyl mercuric acetate, endothal, biuret, technical chlordane, dimethyl 2,3,5,6-tetrachloroterephthalate, diquat, erbon, DNC, DNBP, dichlobenil, DPA, diphenamid, dipropalin, trifluralin, solan, dicryl, merphos, DMPA, DSMA, MSMA, potassium azide, acrolein, benefin, bensulide, AMS, bromacil, 2-(3,4-dichlorophenyl)-4-methyl-1,2,4-oxadiazolidine-3,5-dione, bromoxynil, cacodylic acid, CMA, CPMF, cypromid, DCB, DCPA, dichlone, diphenatril, DMTT, DNAP, EBEP, EXD, HCA, ioxynil, IPX, isocil, potassium cyanate, MAA, MAMA, MCPES, MCPP, MH, molinate, NPA, OCH, paraquat, PCP, picloram, DPA, PCA, pyrichlor, sesone, terbacil, terbutol, TCBA, brominil, CP-50144, H-176-1, H-732, M-2901, planavin, sodium tetraborate, calcium cyanamid, DEF, ethyl xanthogen disulfide, sindone, sindone B, propanil and the like. Such herbicides can also be used in the methods and compositions of this invention in the form of their salts, esters, amides, and other derivatives whenever applicable to the particular parent compounds.

Weeds are undesirable plants growing where they are not wanted, having no economic value, and interfering with the production of cultivated crops, with the growing of ornamental plants, or with the welfare of livestock. Many types of weeds are known, including annuals such as pigweed, lambsquarters, foxtail, crabgrass, wild mustard, field pennycress, ryegrass, goose grass, chickweed, wild oats, velvetleaf, purslane, barnyardgrass, smartweed, knotweed, cocklebur, wild buckwheat, kochia, medic, corn cockle, ragweed, sowthistle, coffeeweed, croton, cuphea, dodder, fumitory, groundsel, hemp nettle, knawel, spurge, spurry, emex, jungle rice, pondweed, dog fennel, carpetweed, morningglory, bed-straw, ducksalad, naiad, cheatgrass, fall panicum, jimsonweed, witchgrass, switchgrass, watergrass, teaweed, wild turnip and sprangletop; biennials such as wild carrot, matricaria, wild barley, campion, chamomile, burdock, mullein, round-leaved mallow, bull thistle, hounds-tongue, moth mullein and purple star thistle; or perennials such as white cockle, perennial ryegrass, quackgrass, Johnsongrass, Canada thistle, hedge bindweed, Bermuda grass, sheep sorrel, curly dock, nutgrass, field chickweed, dandelion, campanula, field bindweed, Russian knapweed, mesquite, toadflax, yarrow, aster, gromwell, horsetail, ironweed, sesbania, bulrush, cattail, winter-cress, horsenettle, nutsedge, milkweed and sicklepod.

Similarly, such weeds can be classified as broadleaf or grassy weeds. It is economically desirable to control the growth of such weeds without damaging beneficial plants or livestock.

The new compounds of this invention are particularly valuable for weed control because they are toxic to many species and groups of weeds. The exact amount of compound required will depend on a variety of factors, including the hardiness of the particular weed species, weather, type of soil, method of application, the kind of beneficial plants in the same area and the like. Thus, while the application of up to only about 1 or 2 ounces of active compound per acre may be sufficient for good control of a light infestation of weeds growing under adverse conditions, the application of 10 pounds or more of an active compound per acre may be required for good control of a dense infestation of hardy perennial weeds growing under favorable conditions.

The herbicidal activity of the new compounds of this invention can be illustrated by many of the established testing techniques known to the art, such as pre- and post-emergence testing.

The herbicidal activity of the compounds of this invention can be demonstrated by experiments carried out for the pre-emergence control of a variety of weeds. In these experiments small plastic greenhouse pots filled with dry soil are seeded with the various weed seeds. Twenty-four hours or less after seeding the pots are sprayed with water until the soil is wet and the test compounds formulated as aqueous emulsions of acetone solutions containing emulsifiers are sprayed at various concentrations on the surface of the soil.

After spraying, the soil containers are placed in the greenhouse and provided with supplementary heat as required and daily or more frequent watering. The plants are maintained under these conditions for a period of 21 days, at which time the condition of the plants and the degree of injury to the plants can be rated on a scale of from 0 to 10, as follows: 0 = no injury, 1,2 = slight injury, 3,4 = moderate injury, 5,6 = moderate severe injury, 7,8,9 = severe injury and 10 = death.

The herbicidal activity of the compounds of this invention can also be demonstrated by experiments carried out for the post-emergence control of a variety of weeds. In these experiments the compounds to be tested are formulated as aqueous emulsions and sprayed at the indicated dosage on the foliage of weeds that have attained a prescribed size. After spraying, the plants are placed in a greenhouse and watered daily or more frequently. Water is not applied to the foliage of the treated plants. The severity of the injury can be determined 14 days after treatment and rated on the scale of from 0 to 10 heretofore described.

We claim:

1. A compound of the formula

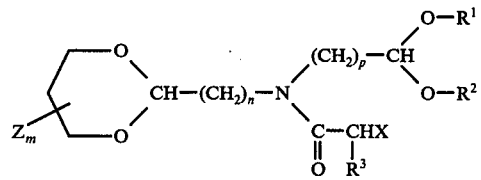

wherein Z is lower alkyl; $m$ is an integer from 0 to 4; $n$ and $p$ are each integers from 1 to 2; $R^1$ and $R^2$ are each lower alkyl; $R^3$ is hydrogen or lower alkyl; and X is halogen.

2. The compound of claim 1, N-(2,2-diethoxyethyl)-N-(1,3-dioxan-2-ylmethyl)-α-chloroacetamide.

3. The compound of claim 1, N-(2,2-dipropoxyethyl)-N-(4-methyl-1,3-dioxan-2-ylmethyl)-α-chloroacetamide.

4. The compound of claim 1, N-(2-methoxy-2-ethoxyethyl)-N-(1,3-dioxan-2-ylmethyl)-α-chloroacetamide.

5. The compound of claim 1, N-(2,2-dibutoxyethyl)-N-(4,5-dimethyl-1,3-dioxan-2-ylmethyl)-α-chloroacetamide.

6. The compound of claim 1, N-(2,2-dihexyloxyethyl)-N-(4-isopropyl-1,3-dioxan-2-ylethyl)-α-chloropropionanamide.

7. The compound of claim 1, N-(3,3-diethoxypropyl)-N-(1,3-dioxan-2-ylmethyl)-α-bromoacetamide.

8. The compound of claim 1, N-(2,2-diethoxyethyl)-N-(1,3-dioxan-2-ylmethyl)-α-chlorobutanamide.

9. The compound of claim 1, N-(2,2-dibutoxyethyl)-N-(4-ethyl-1,3-dioxan-2-ylmethyl)-α-chloroacetamide.

* * * * *